United States Patent [19]
Subramanyam et al.

[11] Patent Number: 5,436,366
[45] Date of Patent: Jul. 25, 1995

[54] PROCESS AND COMPOSITION

[75] Inventors: Ravi Subramanyam, North Brunswick; Suman K. Chopra, Dayton, both of N.J.

[73] Assignee: Colgate-Palmolive Company, Piscataway, N.J.

[21] Appl. No.: 137,450

[22] Filed: Oct. 15, 1993

[51] Int. Cl.⁶ .......................................... C07C 303/32
[52] U.S. Cl. .................................... 562/108; 562/110
[58] Field of Search ................................ 562/108, 110

[56] References Cited
U.S. PATENT DOCUMENTS

| | | | |
|---|---|---|---|
| 2,989,547 | 6/1961 | Whyte | 549/555 |
| 3,024,273 | 3/1962 | Whyte et al. | 562/103 |
| 3,228,979 | 1/1966 | Gaertner | 562/42 |
| 4,502,538 | 3/1985 | Wellington et al. | 166/252 |

OTHER PUBLICATIONS

Whyte, David; Alkyl Glyceryl Ether Sulfonates, Surfactant Science Series, vol. 7, Anionic Surfactants Parts 2, (7) 1976; pp. 483–494.

Primary Examiner—José G. Dees
Assistant Examiner—Joseph M. Conrad, III
Attorney, Agent, or Firm—Martin B. Barancik; Robert C. Sullivan

[57] ABSTRACT

A process for preparing an alkoxylated alkyl glyceryl ether sulfonate which comprises reacting a terminal glycidate (epoxy) of the structure $$R(OCH_2CHR^1)_nOCH_2\underset{O}{\underset{\diagdown\diagup}{CHCH_2}}$$

with a sulfite salt, a bisulfite salt or a sulfite/bisulfite salt mixture at a temperature at or below about 110° C. wherein R is an alkyl or alkenyl of 10 to 20 carbon atoms, inclusive, R' is hydrogen or methyl and n is an integer having an average value of 1 to 10 and obtaining the sulfonate of the structure $$R(OCH_2CHR^1)_nOCH_2CHOHCH_2SO_3^-$$

23 Claims, No Drawings

PROCESS AND COMPOSITION

BACKGROUND OF THE INVENTION

Alkyl glyceryl ether sulfonate salts, (AGES) particularly the sodium salt, have been well known for their commercial utility in detergent compositions for many years. The synthesis of these materials is relatively straight forward and also known for many years. A review article by David Whyte entitled "Alkyl Glyceryl Ether Sulfonates" appearing in Surfactant Science Series, Vol 7, Anionic Surfactants Part 2, 1976 provides a good summary of synthetic routes. In one synthesis a long chain alcohol is reacted with epichlorohydrin under acid catalysis to form a chlorohydrin ether. Thereafter the chlorohydrin ether is subjected to the Strecker reaction, using sodium sulfite, or bisulfite or a mixture thereof, to form the alkyl glyceryl ether sulfonate salt. Since the Strecker reaction is two phase, good interphase contact is required as well as an appropriate catalyst according to the Whyte article. The reaction product is a viscous paste and heat transfer is poor. Therefore the water content in the system is a major means of control of peak reaction temperature as well as the system processability, particularly viscosity, by means of the mixing apparatus. Excessive amounts of water lead to undesirably dilute AGES products. Too little water results in high viscosity, low thermal capacity, and a difficulty controlled exothermic temperature rise. For AGES with an alkyl chain in the $C_{12}$ range an overall water content of 50% or more is suggested for the sodium salt. The greater solubility of potassium sulfite and potassium salts of AGES allows somewhat higher solid levels to be about 60% employed.

Another route to AGES mentioned in the Whyte article is sulfonating a terminal glycidate epoxy ether of the desired structure with a mixture of sulfite and bisulfite salt as shown below.

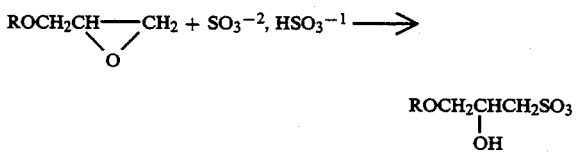

An even higher solids content can be achieved in this sulfonation reaction of the epoxide according to the review article. However the review article states that difficulties in temperature control and excessive product viscosities make it undesirable to achieve these higher solid levels. In fact high temperatures are used to initiate the sulfonation of the epoxide with the sulfite-bisulfite mixture, 300° F. or less. The lowest temperature used for iinitiation of the sulfonation of the epoxy in Whyte U.S. Pat. No. 2,989,547 is 275° F., Example 6. In each of the examples in this patent, the continuing reaction is carried out at a significantly higher temperature than the initiation temperature.

Alkoxylated alkyl glyceryl ether sulfonates, hereinafter referred to as NEGS, have been known for many years as well and are disclosed to be useful in secondary recovery processes for increasing production in oil wells. The difference between AGES and NEGS is the presence of one or more alkoxy groups between the last carbon atom of the alkyl group and the oxygen atom of AGES. NEGS is depicted below as the ethoxylated sodium salt.

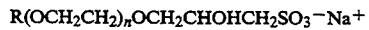

n is an integer of one or more.
R is an alkyl or alkenyl group

The synthesis of AGES outlined above involves functional group transformation, the conversion of an epoxide to a hydroxy sulfonate. Since the same functional group transformation occurs in the preparation of NEGS, the advantages and disadvantages occurring in the AGES synthesis outlined above would also be expected in a NEGS synthesis using the same process.

Surprisingly this does not occur to the extent expected. Rather, several significant advantages occur when the ethoxylated alkyl terminal epoxy is reacted preferably with a mixture of sulfite-bisulfite salt.

Firstly, the reaction can be carried out at room temperature or elevated temperature below 100° C., the boiling point of water, without the use of elevated pressure. This brings about lower processing costs and allows the surfactant to be made in the same type of "kettle" or "crutcher" like equipment in which a personal cleansing composition can be prepared. For the synthesis of AGES, a substantially elevated temperature, below about 300° F., is used to initiate the sulfonation conversion of the glycidate to the hydroxy sulfonate structure via the sulfite-bisulfite reaction. However this present conversion of the NEGS glycidate is initiated and proceeds to completion at temperatures which are at or below the boiling point of water. In fact, even though the reaction is exothermic, the reaction temperature can be maintained at or below about 110° C., preferably at or below 100° C. Such lower temperatures do not require the presence of super atmospheric pressure to maintain the appropriate quantity of water during the reaction or the addition of water.

Secondly, when converting the glycidate of AGES with sodium sulfite-bisulfite, the viscosity increases as the percent solids of products increases according to the cautionary statements of the Whyte article. However, when preparing NEGS from the terminal glycidate (epoxy) starting material the viscosity of the reaction mass measured at completion of the reaction of from about 50 wt % to 70 wt % solids content remains essentially unchanged or is reduced. This is an important factor in allowing preparation of a higher percentage NEGS product in water. Such a high solids content provides major advantages in handling, cost savings in transport, and processing the NEGS through adequate mixing into a personal cleansing composition.

Thirdly, the sodium salt(s) of a sulfite-bisulfite mixture can be employed and still see the higher solids, processable composition. Such higher solids content was previously thought to be achievable or potentially achievable only through the use of the potassium salt according to the review article. However potassium salts of a surfactant brings about a much softer and difficult to process solid personal cleansing composition than a sodium salt composition.

Fourthly, a catalytic quantity of a catalyst preferably an emulsifying agent, in the NEGS reaction brings about a shorter induction time and shortened total reaction time than the similar or same agent employed in a comparable AGES reaction.

SUMMARY OF THE INVENTION

In accordance with the invention, there is a process for preparing an alkoxylated alkyl glyceryl ether sulfonate which comprises reacting a terminal glycidate (epoxy) of the structure

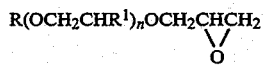

with a sulfite/bisulfite salt mixture at a temperature at or below about 110° C. wherein R is an alkyl or alkenyl of 10 to 20 carbon atoms, inclusive, R' is hydrogen or methyl and n is an integer having an average value of 1 to 10 and obtaining the sulfonate of the structure

DETAILED DESCRIPTION OF THE INVENTION

The preparation of a salt of an alkoxylated, preferably ethoxy, alkyl glyceryl ether sulfonate from a terminal glycidate (epoxy) starting material by the use of a sulfite bisulfite salt mixture proceeds smoothly, economically and with significant advantages over the preparation of AGES from the comparable terminal glycidate starting material. The NEGS can be prepared in a high solids concentration at a lower temperature over a shorter time period and with a shorter induction period than AGES.

In the terminal glycidate starting material and product above, R' is preferably hydrogen, n is preferably 1 to 4, more preferably 1 or 2, and R is preferably 12 to 15 carbon atoms, inclusive and is preferably normal than branched. Alkyl is preferred.

The temperature at which the sulfonation reaction of the glycidate occurs is at a temperature at or below 100° C., the boiling point of water. Temperatures can be as low as room temperature, if desired, however, the uncatalyzed reaction is quite slow at that point. Generally, a temperature range of about 50 to 99° C., preferably about 75 to 95° C. brings about a well-controlled, speedy reaction for maximum yields in a minimum amount of time.

Temperatures as high as 110° C. can be employed, particularly if the water amount is to be reduced somewhat. Super atmospheric pressure need not be employed in the reaction. In Whyte U.S. Pat. No. 2,989,547 the temperature used to promote the sulfonation of the AGES glycidate was disclosed to be about 149° C. (300° F.) In general. The lowest temperature for initiation of the reaction was reported to be 135° C. (275° F.); see Example 6, column 7. After the induction of reaction, the temperature always went higher because of the exothermic nature of the reaction. The preparation of NEGS is also exothermic but temperatures are readily maintained at or below 110° C., preferably at or below 100° C.

The sulfonating agent employed is a sulfite salt, bisulfite salt or a mixture of sulfite and bisulfite salts. The ratios of the two salts can vary from about 0.1 to 35 wt % of the sulfite, the remainder being bisulfite, preferably about 22 to 30 wt % of the sulfite. The cation of the salt is any metal or ammonium ion which brings about water solubility for the sulfite-bisulfite mixture. Examples of such cations are sodium, potassium, ammonium and alkylol substituted ammonium. Sodium and potassium are preferred. An excess of the salt is preferably used in the reaction. Potassium sulfite-bisulfite salts are more soluble in an aqueous media than the sodium salts according to the Whyte review article. However, the potassium salts of a surfactant, in this case the ethoxylated alkyl glyceryl ether sulfonate, when used in a solid cleansing composition, brings about a composition which is difficult to process and use as a bar because of the softness of the composition.

Still further, it has been surprisingly found that very high solids content of NEGS in water can be achieved. Over a range of about 50 to 70% solids content of NEGS, measured at the reaction completion, the viscosity of the reaction mass does not increase with increasing solids content. Rather, the viscosity levels off or decreases over this range allowing a higher active ingredient (A.I.) concentration to be achieved while still maintaining the processability (stirrability) of the reaction mass and proper control of the exothermic reaction. As noted in the Whyte review article relating to the synthesis of AGES, above 60% solids content can be achieved with potassium salt but difficulties in temperature control and excessive product viscosities make it undesirable to achieve these higher solids levels. Such product solids content levels are achieved with this invention while maintaining readily processable reaction viscosities and good temperature control. Still, even more surprising, these high solids contents are obtained while using the sodium salt of the sulfite-bisulfite mixture.

Although the kinetics of the reaction are generally satisfactory, the presence of a catalyst to overcome or shorten the initial induction period is preferred. It has been found that small quantities of a material that brings about an emulsification of the aqueous phase of the salt and the organic phase of the glycidate (epoxy) starting materials substantially shortens the overall time period of the synthesis and the induction period as well. In fact, surprisingly an uncatalyzed NEGS synthesis proceeds to completion at a faster rate than a NEGS catalyzed AGES synthesis. Interestingly AGES synthesis catalyzed by NEGS proceeds faster than an AGES synthesis catalyzed by AGES, both being slower than an uncatalyzed NEGS synthesis. Of course the catalyzed NEGS process is even faster. Any material which aids in the forming of an emulsion of the phases can be used as a catalyst. Examples of such materials include the product of the reaction or analogue (NEGS), AGES, soap, anionic surfactant such as a sulfate, sulfonate, sarcosinate and the like. Nonionic surfactants which are emulsifiers can also be employed. Quantities of the catalyst are not unduly significant and, by definition a catalytic quantity is effective. This may vary from about 0.1 to about 10 wt % of the reaction mass, preferably about 1–5 wt %.

A further benefit of the mild conditions of this process is that the NEGS can be synthesized in the same equipment that personal cleansing compositions are prepared. A simple crutcher or kettle can be employed as the reaction vessel. Readily available steam can be employed as the heating medium. Thereafter the usual soap making procedures can be followed for making a liquid or solid cleansing composition containing NEGS. As stated previously the use of the sodium salts allows the preparation a solid hard solid cleansing composition. Additional surfactants can be added to the cleansing composition preparation process such as soap, anionic, nonionics, zwitterionics, amphoterics and the like.

Below are examples and data of the invention and comparative examples showing the advantages of the inventive process and composition. These examples are intended to exemplify the broad inventive concept and not limit such concept.

In these examples, the glycidate employed is one where R is normal alkyl of fourteen to fifteen carbon atoms. When making NEGS, the glycidate has R' as hydrogen and n as an average value of 1. The percent active ingredient (AI) product is measured at reaction completion by a two phase titration using methylene blue as indicator. After synthesis was complete, a 0.4 g sample of acid mixture was accurately weighed in a 100 ml beaker and was dissolved in deionized water. The solution was transferred to a volumetric flask and made up to 100 ml with deionized water. An aliquot (10 ml) of this solution was mixed with 25 ml of methylene blue indicator and 15 ml of chloroform in a 100 ml glass stoppered mixing cylinder. The mixture was titrated with Benzethonium Chloride solution (Hyamine 1622) while using vigorous agitation. The end point was reached when the aqueous layer was more blue than the organic layer (upon the addition of a 0.05 ml increment). The sample size was apportioned such that 6–14 ml of 0.004842 N Benzethonium Chloride solution was required for the titration.

Active ingredient levels (% AI) in the samples were calculated using the following equation:

$$\% \text{ AI} = \frac{(\text{ml Hyamine} - .05 \times N \text{ Hyamine} \times MW \times 100}{\text{wt. of sample in aliquot} \times 1000}$$

An additional benefit of the reaction is that the amount of "free oil", nonionic material, at the end of the reaction is quite low.

EXAMPLE 1

Synthesis of NEGS wherein n is an average value of one, R' is hydrogen, and R is normal alkyl of fourteen or fifteen carbon atoms (approx. 3% NEGS catalyst).

A mixture of sodium sulfite (14.4 g, 0.114 moles) and sodium bisulfite (35.68 g. 0.243 moles) was dissolved in 72.5 gms of distilled water in a thick walled glass reactor equipped with a water cooled condenser. To the above solution glycidate (epoxy) (157.1 g, 0.42 moles) was added. An anionic surfactant, alkylethoxylated-glycerylethersulfonate, having the same values of R and n as the glycidate (30 g, 33% active ingredient, moisture 58.4%, approx. 3wt %) was added as the catalyst to intitiate the reaction. The reaction mixture was heated to 95 C., 1 atm. pressure and stirred at 200–300 rpm. The reaction was monitored along its course by the earlier identified titration method. Under these reaction conditions, it took 4 hours for the completion of the reaction, and 95% of the glycidate was converted to the sodium salt of alkylethoxylatedglycerylsulfonate surfactant (NEGS) product.

Analysis: % AI 62.3,% Moisture 29 and % free oil 9.4 (based on 100% AI)

EXAMPLE 2

Synthesis of NEGS (uncatalyzed)

Sodium sulfite (14.4 g, 0.114 moles), sodium bisfulfite (35.7 g, 0.343 moles) glycidate identified in Example 1 (157.0 g, 0.424 moles) and 90 g of distilled water were weighed and added to the reaction. The same procedure as mentioned above in Example 1 was used except no NEGS catalyst was used. It took more than 6 hours for the completion of the reaction and 93% of the glycidate was converted to NEGS.

Analysis: % AI 59.7, % moisture 30 and % free oil 9.98 (based on 100% AI)

COMPARATIVE EXAMPLE 1

Synthesis of AGES (product solids, approx. 3% NEGS catalyst)

Sodium sulfite (14.4 g, 0.114 moles), sodium bisulfite (35.7 g, 0.343 moles) were dissolved in 72.2 g of distilled water. Nonethoxylated Glycidate (with an alkyl chain of 14 and 15 carbon atoms (137.3 g, 0.425 moles) was added. NEGS as defined in Example 1 (32.3 g, % AI 33.3,% moisture 58.4, approx. 3% by weight) was added as the catalyst. The reaction rate was substantially slower than the catalyzed NEGS reaction of Example 1. It took 7 hours for the reaction to complete, and 95% of the glycidate was converted to alkylglycerylethersulfonate (AGES).

Analysis: % AI 59, moisture 31% and % free oil 9.2 (based on 100% AI).

COMPARATIVE EXAMPLE 2

Synthesis of AGES (uncatalyzed)

Sodium sulfite (14.4 g, 0.114), sodium bisulfite (35.7 g, 0.343 moles) were dissolved in 90.9 g of distilled water and glycidate as in comparative Example 1 (137.3 g, 0.125 mole) was added. The same procedure as described in Example 1 was used. The reaction was very slow and in 7 hours only 2% of the glycidate was converted into AGES.

Analysis: % AI 2.02, % moisture 32 and free oil 65.9% (based on 100% AI).

EXAMPLE 3

NEGS (3% soap 85/15 tallow/coco as catalyst)

Sodium sulfite (14.4 g, 0.114 moles), sodium bisulfite (35.7 g, 0.343 moles) were dissolved in 85.5 g of distilled water. Glycidate of example 1 (157 g, 0.424 moles) was added. Soap (85/15, tallow/coco; moisture 30%, approx. 3% by weight) was added as the catalyst. The reaction was faster than the uncatalyzed NEGS reaction; however it was slower than the NEGS catalyzed reaction. After 7 hours, 86.2% of the glycidate was converted to NEGS.

Analysis: % AI 53.5 and % moisture 29.

The results are summarized in the Table below.

| Example | Product | 3% Catalyst | Reaction Time, Hours | % Glycidate Converted to Product |
| --- | --- | --- | --- | --- |
| 1 | NEGS | Yes | 4 | 95 |
| 2 | NEGS | No | 6+ | 93 |
| Comp 1 | AGES | Yes | 7 | 95 |
| Comp 2 | AGES | No | 7 | 2 |

The superiority of the process for preparing NEGS over the same process parameters in preparing AGES is clear. Even the uncatalyzed NEGS reaction is faster than the catalyzed AGES reaction.

EXAMPLE 4

Various NEGS reactions were carried out to provide differing concentrations of Active Ingredient (AI), in the product. This concentration of AI is also referred to as percent solids content. At the completion of the reaction the AI (% solid content) was assayed and the viscosity of the reaction mass measured on a Carrimed Rheometer by TA Instrument. The viscosity was measured at various shear rates, the shear rates being varied by the Rheometer. Below are the results.

| Solids Content (AI) % | Shear Rate, sec$^{-1}$ | Viscosity, Pa.s. |
|---|---|---|
| 33 | 22.76 | 5.33 |
| 44 | 23.17 | 11.28 |
| 50 | 23.19 | 13.98 |
| 65 | 24.49 | 6.55 |
| 33 | 43.85 | 3.64 |
| 44 | 43.99 | 7.97 |
| 50 | 44.17 | 8.33 |
| 65 | 43.47 | 4.94 |
| 33 | 74.21 | 2.48 |
| 44 | 69.83 | 3.73 |
| 50 | 71.60 | 5.36 |
| 65 | 72.56 | 4.94 |

This data shows that as the solids content increases at the same shear rate, the viscosity increases until about 50%; thereafter, up to at least 65% solids content, the viscosity is reduced or at least levels off.

We claim:

1. A process for preparing an alkoxylated alkyl glyceryl ether sulfonate which comprises reacting a terminal glycidate (epoxy) of the structure $$R(OCH_2CHR^1)_nOCH_2CHCH_2 \atop \underset{O}{\diagdown \diagup}$$

with a bisulfite or a sulfite bisulfite salt mixture at a temperature at or below about 110° C., at atmospheric pressure and the solvent consisting essentially of water wherein R is an alkyl of 10 to 20 carbon atoms, inclusive, R' is hydrogen or methyl and n is an integer having an average value of 1 to 10 and obtaining a salt of the sulfonate of the structure $$R(OCH_2CHR^1)_nOCH_2CHOHCH_2SO_3^-$$

2. The process in accordance with claim 1 wherein R' is hydrogen and n is an integer of average value of one to four.

3. The process in accordance with claim 2 wherein the temperature is equal to or below about 100° C.

4. The process in accordance with claim 3 wherein the temperature is at least room temperature.

5. The process in accordance with claim 4 wherein the temperature is at least about 50° C.

6. The process in accordance with claims 1 and 2 wherein R is twelve to fifteen carbon atoms, inclusive.

7. The process in accordance with claim 6 wherein R is normal.

8. The process in accordance with claim 5 wherein the cation of the sulfite bisulfite mixture is sodium or potassium.

9. The process in accordance with claim 8 wherein the cation is sodium.

10. The process in accordance with claim 9 wherein the wt. % of sulfite in the bisulfite sulfite mixture is about 0.1 to 35 wt %.

11. The process in accordance with claim 5 wherein the solids content of the reaction mass after completion of conversion of the glycidate to the sulfonated product is from about 40 to 75 wt % of the reaction mass.

12. The process in accordance with claim 11 wherein the solids content is from about 50 to 70 wt %.

13. The process in accordance with claims 1, 2 or 5 wherein the $R(OCH_2CHR^1)_nOCH_2CHOHCH_2SO_3^-$ prepared in claim 1 is further processed into a personal cleansing composition.

14. The process in accordance with claim 13 wherein the personal cleansing composition is in bar form.

15. The process in accordance with claim 14 wherein the counterion of the salt is sodium.

16. The process in accordance with claims 1 or 2 wherein the process is carried out in equipment which is normally employed in making soap.

17. The process in accordance with claim 16 wherein the equipment in which the process is carried out is a kettle or crutcher.

18. The process in accordance with claim 17 wherein the equipment is a crutcher.

19. The process in accordance with claims 1 or 2 wherein a catalyst is used in the process in quantities to reduce the induction time of the reaction.

20. The process in accordance with claim 12 wherein the catalyst helps to bring about emulsification of an aqueous phase and an organic phase.

21. The process in accordance with claim 20 wherein the catalyst is an anionic surfactant.

22. The process in accordance with claim 21 wherein the surfactant is selected from the group consisting of the product of claim 1, soap, an alkyl glyceryl ether sulfonate or a mixture of two or more of these surfactants.

23. A process which comprises reaction of a glycidate of the formula $$ROCH_2CHCH_2 \atop \underset{O}{\diagdown \diagup}$$

wherein R is an alkyl or alkenyl of 10 to 20 carbon atoms with a sulfite salt, bisulfite salt or a mixture of sulfite bisulfite salt in the presence of catalytic quantities of a salt of a sulfonate of the formula $$R_1(OCH_2CHR^1)_nOCH_2CHOHCH_2SO_3^-$$

wherein $R_1$ is alkyl or alkenyl of 10 to 20 carbon atoms, $R^1$ is hydrogen or methyl and n is an integer of average value 1 to 10.

* * * * *